(12) United States Patent
Ishikura et al.

(10) Patent No.: US 8,926,645 B2
(45) Date of Patent: Jan. 6, 2015

(54) DISPOSABLE LANCING DEVICE

(71) Applicant: Nipro Corporation, Osaka-shi, Osaka (JP)

(72) Inventors: Kohzo Ishikura, Osaka (JP); Tomohiro Uchimura, Osaka (JP); Ken Suzuki, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 13/864,859

(22) Filed: Apr. 17, 2013

(65) Prior Publication Data

US 2013/0238007 A1    Sep. 12, 2013

Related U.S. Application Data

(63) Continuation of application No. 13/014,330, filed on Jan. 26, 2011, now Pat. No. 8,439,941.

(30) Foreign Application Priority Data

Jun. 22, 2010  (JP) .................. 2010-141526

(51) Int. Cl.
 *A61B 17/34*    (2006.01)
 *A61B 5/151*    (2006.01)
 *A61B 5/15*    (2006.01)

(52) U.S. Cl.
 CPC ........... *A61B 5/15144* (2013.01); *A61B 5/1411* (2013.01); *A61B 5/15142* (2013.01)
 USPC ....................................................... 606/181

(58) Field of Classification Search
 USPC .......... 606/181, 182, 186, 167; 600/583, 573; 604/22, 117, 110, 207–211
 See application file for complete search history.

(56) References Cited

U.S. PATENT DOCUMENTS

| | | |
|---|---|---|
| 5,366,470 A | 11/1994 | Ramel |
| 5,554,166 A | 9/1996 | Lange et al. |
| 5,755,733 A | 5/1998 | Morita |

(Continued)

FOREIGN PATENT DOCUMENTS

| | | |
|---|---|---|
| JP | A-7-16218 | 1/1995 |
| WO | WO 2005/110227 A1 | 11/2005 |
| WO | WO 2010/002072 A1 | 1/2010 |

OTHER PUBLICATIONS

Japanese Office Action issued in Japanese Patent Application No. 2010-141526 dated Nov. 29, 2013 (w/ partial translation).

(Continued)

*Primary Examiner* — Ryan Severson
*Assistant Examiner* — Anh Dang
(74) *Attorney, Agent, or Firm* — Oliff PLC

(57) ABSTRACT

A disposable lancing device including: a lancet housed in a housing and urged by a spring member such that a puncture member provided at a distal end of the lancet is adapted to extend out from the housing so as to carry out a puncturing operation; a locking ring disposed within the housing such that the lancet is allowed to displace in an extension direction through the locking ring; a locking protrusion provided to the lancet and adapted to be engaged by the locking ring so as to hold the lancet in a puncture-ready position located deep in the housing with the spring member being compressed; and an operating member adapted to carry out the puncturing operation by rotating the locking ring so as to disengage the locking protrusion from the locking ring and displace the lancet in the extension direction by means of the spring member.

7 Claims, 17 Drawing Sheets

(56) References Cited

U.S. PATENT DOCUMENTS

| | | |
|---|---|---|
| 6,764,496 B2 | 7/2004 | Schraga |
| 7,175,643 B2 | 2/2007 | Shi |
| 7,238,192 B2 | 7/2007 | List et al. |
| 2005/0070945 A1 | 3/2005 | Schraga |
| 2007/0010841 A1 | 1/2007 | Teo et al. |
| 2007/0135828 A1 | 6/2007 | Rutynowski |
| 2007/0225742 A1 | 9/2007 | Abe et al. |
| 2008/0045992 A1 | 2/2008 | Schraga |
| 2008/0082116 A1 | 4/2008 | Lathrop et al. |
| 2008/0109025 A1 | 5/2008 | Yang et al. |

OTHER PUBLICATIONS

European Search Report dated Sep. 29, 2011 issued in European Patent Application No. 11 17 0969.7.

Chinese Office Action issued in Chinese Patent Application No. 201110179810.4 dated Mar. 3, 2014 (w/ translation).

Jul. 30, 2014 Office Action issued in Chinese Patent Application No. 201110179810.4 (with translation).

STANDARD CONDITION

STANDARD CONDITION

STANDARD CONDITION

STANDARD CONDITION / PUNCTURE-READY CONDITION
(REAR VIEW)

STANDARD CONDITION / PUNCTURE-READY CONDITION
(FRONT VIEW)

PUNCTURE-READY CONDITION

PUNCTURE-READY CONDITION

PUNCTURING OPERATION CONDITION
AND POST-PUNCTURE CONDITION (REAR VIEW)

PUNCTURING OPERATION CONDITION
AND POST-PUNCTURE CONDITION (FRONT VIEW)

PUNCTURING OPERATION CONDITION
(AT THE INSTANT OF PUNCTURE)

PUNCTURING OPERATION CONDITION
(AT THE INSTANT OF PUNCTURE)

POST-PUNCTURE CONDITION

POST-PUNCTURE CONDITION

PREVENTION OF REUSE

PREVENTION OF REUSE

STANDARD CONDITION / PUNCTURE-READY CONDITION
(REAR VIEW)

PUNCTURE-READY CONDITION (REAR PERSPECTIVE VIEW)

PUNCTURE-READY CONDITION

PUNCTURING OPERATION CONDITION AND
POST-PUNCTURE CONDITION (REAR VIEW)

PUNCTURING OPERATION CONDITION
(REAR PERSPECTIVE VIEW)

PUNCTURING OPERATION CONDITION
(AT THE INSTANT OF PUNCTURE)

POST-PUNCTURE CONDITION

PREVENTION OF REUSE

PREVENTION OF REUSE

DISPOSABLE LANCING DEVICE

This is a Continuation of application Ser. No. 13/014,330 filed Jan. 26, 2011. The disclosure of the prior application is hereby incorporated by reference herein in its entirety.

INCORPORATED BY REFERENCE

The disclosure of Japanese Patent Application No. 2010-141526 filed on Jun. 22, 2010 including the specification, drawings and abstract is incorporated herein by reference in its entirety.

BACKGROUND OF THE INVENTION

1. Field of the Invention

The present invention relates in general to a lancing device used to lance or puncture the skin and collect a small quantity of blood, and in particular to a disposable lancing device intended to be discarded after a single use.

2. Description of the Related Art

Self-collection of small quantities of blood is sometimes necessary for medical purposes. For example, for patients with diabetes, it is necessary for the patient himself to regularly collect his own blood in order to periodically check blood sugar level (Self-Monitoring of Blood Glucose: SMBG). Lancing devices have been in use for some time to enable such self-collection of blood to be carried out safely and dependably. In particular, for the purpose of preventing infection, lancing devices of disposable type designed to be discarded after a single use have been available in the past.

Such lancing devices typically include a lancet housed within a housing and urged by a spring member, and are designed to carry out the puncturing operation by extending a puncture member provided to the distal end of the lancet out from the housing. Specifically, as disclosed in U.S. Publication No. US 2007/0135828, the instrument is designed to be used by pushing an operating member with a lancet engaged within the housing, so that a spring member disposed deeper than the lancet experiences compressive deformation. When compression force of the spring member increases to such an extent as to disengage the lancet, the lancet will extend out from the housing to carry out the puncturing operation.

However, with the lancing devices of this conventional construction, it is difficult to establish compression force of the spring member that is required to disengage the lancet from the housing with sufficient accuracy. Consequently, there may be a case where, even though the spring member is not sufficiently compressed, the lancet might disengage to induce the puncturing operation, so that insufficient puncturing force causes shortage of exuded blood. There may be another case, on the contrary, where even if the operating member is firmly pushed, the lancet might fail to disengage, making it difficult to bring about the puncturing operation.

International Publication No. WO 2005/110227 and U.S. Pat. No. 5,755,733 disclose a structure in which a push operating member that induces compressive deformation of a spring member is furnished with an abutting portion for releasing engagement, and when the push operating member reaches a prescribed position the abutting portion comes into abutment against and disengage a detent piece of a lancet engaged by a housing. However, with such lancing devices, in addition to force for inducing compressive deformation of the spring member, force for deforming and disengaging the detent piece of the lancet should be exerted on the push operating member, thereby inevitably requiring large operating force.

Meanwhile, U.S. Publication No. US 2007/0225742 and U.S. Publication No. US 2005/0070945 disclose a structure in which a detent piece of a lancet engaged by a housing is designed to be pushed from the horizontal direction so as to release the engagement, thereby carrying out the extending action. However, since the detent piece of the lancet is subjected to pushing force from the horizontal direction, the center axis of the lancet may deviate to catch other components, or the lancet may be pressed against the other components to increase frictional resistance during the extending action, posing a risk of impaired movement of the lancet during the extending action.

Another structure is disclosed in U.S. Pat. No. 7,238,192, in which a lancet is rotatable in the circumferential direction with respect to a housing so that the engagement of the lancet with a seating surface formed to the inner face of the housing is adapted to be released by rotating action of the lancet. However, if the lancet is rotated by exerting rotational force, due to deformation or displacement of the lancet there is a risk of difficulty in duly ensuring release of the engagement or stability of the extending action. In particular, with the lancet urged by a spring member, it is difficult to rotate the lancet alone, posing another risk of inducing deformation of the spring member as well and providing adverse effects on its urging action.

SUMMARY OF THE INVENTION

It is therefore one object of this invention to provide a disposable lancing device of novel construction capable of reliably and stably maintaining the lance-ready or puncture-ready position where the lancet is engaged in a position to which the spring member is compressed, as well as carrying out the puncturing operation through disengagement of the lancet.

A first mode of the present invention provides a disposable lancing device including: a housing; a spring member; a lancet housed in the housing and urged by the spring member such that a puncture member provided at a distal end of the lancet is adapted to extend out from the housing so as to carry out a puncturing operation; a locking ring disposed within the housing such that the lancet is allowed to displace in an extension direction through the locking ring; a locking protrusion provided to the lancet and adapted to be engaged by the locking ring so as to hold the lancet in a puncture-ready position located deep in the housing with the spring member being compressed; and an operating member adapted to carry out the puncturing operation by rotating the locking ring so as to disengage the locking protrusion from the locking ring and displace the lancet in the extension direction by means of the spring member.

The lancing device according to the present mode employs the locking ring as a separate element from the housing and the lancet. By rotating the locking ring, it is possible to disengage the lancet that has been urged by the spring member while being held in the puncture-ready position, thereby carrying out the puncturing operation. Thus, the spring member compressed to the puncture-ready position in advance is able to exert a stable urging force on the lancet and bring about the puncturing operation. In addition, the lancet can avoid being subjected to the operating force for carrying out the puncturing operation from the horizontal direction. Accordingly, catching due to deviation of the center axis of the lancet or increase of frictional force against other components will be prevented, thereby realizing the puncturing operation in a stable manner. Moreover, unlike the lancet urged by the spring member, the locking ring to be rotated can be easily rotated alone, making it possible to readily and stably bring about the puncturing operation.

A second mode of the present invention provides the disposable lancing device according to the first mode wherein subsequent to the puncturing operation, a circumferential position of the locking ring relative to the lancet is maintained so as to hold the locking protrusion of the lancet disengaged from the locking ring so that the locking protrusion is prevented from being re-engaged by the locking ring.

A third mode of the present invention provides the disposable lancing device according to the first or second mode further including a reuse-preventing protrusion provided to the lancet and adapted to prevent the locking protrusion from being re-engaged by the locking ring such that with the locking ring located at a rotational position representing that the locking protrusion has been disengaged and the puncturing operation of the lancet has been carried out, as the lancet is pushed and displaced deep into the housing the reuse-preventing protrusion comes into abutment against the locking ring so as to limit deep displacement of the lancet relative to the locking ring.

With the lancing device according to the present mode, a reuse-preventing mechanism can be realized by utilizing the locking ring. In particular, in view of the locking ring experiencing rotational displacement during the puncturing operation, the reuse-preventing protrusions are provided to the lancet so as to come into abutment against the locking ring at its rotational position subsequent to the puncturing operation. This arrangement makes it possible to realize the mechanism for reliably preventing reuse of the instrument with a small number of parts and a simple structure.

A fourth mode of the present invention provides the disposable lancing device according to the third mode wherein the locking ring is allowed to displace deep into the housing, and with the locking ring located at the rotational position representing that the puncturing operation of the lancet has been carried out, as the lancet is pushed and displaced deep into the housing the reuse-preventing protrusion comes into abutment against the locking ring so that the locking ring experiences deep displacement together with the lancet.

With the lancing device according to the present mode, even if it is attempted by pushing the lancet from the distal end side of the housing to forcibly move the locking protrusion of the lancet deeper past the locking ring and engage it by the locking ring, the locking ring will experience displacement deeper into the housing together with the lancet, thereby more reliably preventing reuse of the instrument A fifth mode of the present invention provides the disposable lancing device according to any of the first to fourth modes further including an inadvertent operation prevention mechanism for inhibiting rotation of the locking ring with respect to the housing.

The lancing device according to the present mode is able to prevent an unexpected puncturing operation by inhibiting the locking ring from rotating. The inhibition of rotation of the locking ring that is not urged in the circumferential direction can easily be realized through a component having lower strength compared to the case, for example, which directly inhibits extension of the lancet urged by the spring means.

A sixth mode of the present invention provides the disposable lancing device according to the fifth mode further including a cap attached to the distal end of the lancet so as to cover the puncture member, wherein with the cap attached, the inadvertent operation prevention mechanism is provided by the locking ring being engaged nonrotatably with respect to the housing via either of the cap and the lancet, and through detachment of the cap the locking ring is adapted to be disengaged to become rotatable.

In the lancing device according to the present mode, the inadvertent operation prevention mechanism is designed to be released by means of the cap being detached when carrying out the puncturing operation. Thus, it is possible to prevent the inadvertent operation prevention mechanism from being improperly released, while allowing the mechanism to be released without needing any special operation when carrying out the puncturing operation.

A seventh mode of the present invention provides the disposable lancing device according to any of the first to sixth modes further including a guide mechanism for guiding the lancet in the extension direction while preventing circumferential displacement of the lancet with respect to the housing.

The lancing device according to the present mode is able to surely prevent interlocked rotation of the lancet in association with rotation of the locking ring, thereby more reliably carrying out the puncturing operation through rotation of the locking ring. Additionally, stability of the puncturing operation through extension of the lancet will be more improved.

According to the present invention, by rotating the locking ring, it is possible to disengage the lancet that has been urged by the spring member while being held in the puncture-ready position, thereby carrying out the puncturing operation. Therefore, the lancet can avoid being subjected to the operating force for carrying out the puncturing operation from the horizontal direction. Accordingly, catching due to deviation of the center axis of the lancet or increase of frictional force against other components will be prevented, thereby realizing a desired puncturing operation in a stable manner.

BRIEF DESCRIPTION OF THE DRAWINGS

The foregoing and/or other objects features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
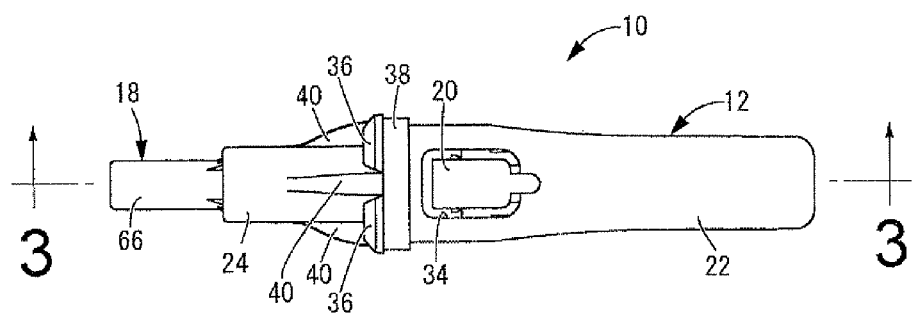
FIG. 1 is a top plane view of a disposable lancing device according to a first embodiment of the present invention in a standard condition.
Figure 2:
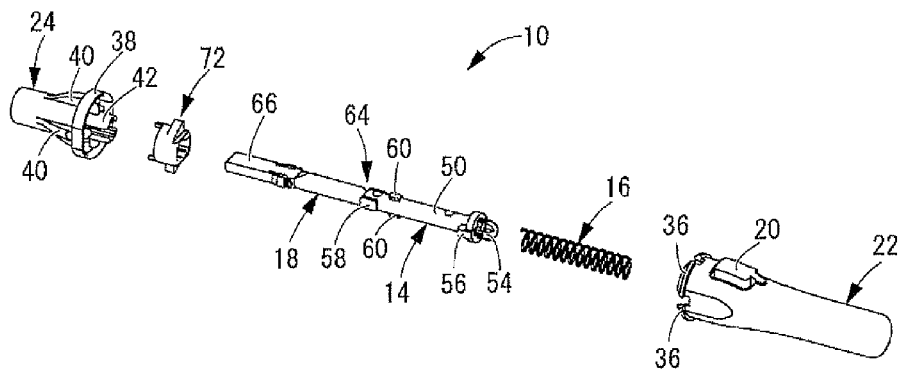
FIG. 2 is an exploded perspective view of the lancing device of FIG. 1.

First, FIG. 1 depicts in plan view a disposable lancing device 10 according to a first embodiment of the present invention, while FIGS. 2 to 5 depict the instrument in exploded perspective view, longitudinal sectional view, and transverse sectional view. FIGS. 1, 3, 4, and 5 all depict the lancing device 10 in the retail product condition (standard condition) in which it is provided to the user. The lancing device 10 includes a lancet 14 and a compression coil spring (serving as a spring member) 16 housed in a housing 12, and is designed to be used by removing a needle cap 18 (serving as a cap) from the lancet 14 and then extending the lancet 14 out from the housing 12 through push operation of an operating element 20, to carry out the lancing or puncturing operation. Unless indicated otherwise, in the following description, center axis direction refers to the center axis direction of the housing 12 and the lancet 14 (the horizontal direction in FIG. 1); the leftward direction in FIG. 1, which represents the extension direction of the lancet 14, refers to the front; and the rightward direction refers to the back.

Turning to a more detailed description, the housing 12 is composed of a housing main body 22 and a housing nose cone 24 each molded from resin. The housing main body 22 has a deep, generally bottomed cylindrical shape, to the mouth of which fixedly attached the housing nose cone 24, which has generally cylindrical shape.

A spring seat 26 is disposed on the basal wall of the housing main body 22 and projects inward from the center of its inside face. A plurality of guide ribs 28 extend in straight lines in the axial direction and protrude up from the inside peripheral face of the cylinder wall of the housing main body 22. The plurality of guide ribs 28 define a pair of guide rails 30, 30 which are situated in opposition in the axis-perpendicular direction on the cylinder wall inside face of the housing main body 22.

The operating element 20 provided as the operating member is formed on the cylinder wall of the housing main body 22 at a location near the mouth section, which is slightly flared relative to the basal wall section. This operating element 20 is arranged within a passage window 34 formed in the peripheral wall of the housing main body 22, and is partially connected to the housing main body 22. When the operating element 20 is pushed with the finger from outside the housing main body 22, the connecting portion experiences elastic deformation so that the operating element 20 is displaced inwardly towards the housing main body 22.

An interlock rib 36 that protrudes up from the outside peripheral face and extends in the circumferential direction is integrally formed at the lip of the mouth of the cylindrical wall of the housing main body 22. Meanwhile, a large-diameter interlock ring 38 extending in the circumferential direction about the outside perimeter is integrally formed at the axial back end of the housing nose cone 24. The interlock ring 38 is connected to and supported on the housing nose cone 24 through connecting leg portions 40 that protrude out at several locations along the circumference of the outside peripheral face of the housing nose cone 24.

The housing nose cone 24 is installed on the housing main body 22 by attaching the housing nose cone 24 to the mouth of the housing main body 22 and interlocking the interlock rib 36 of the housing main body 22 in the interlock ring 38 of the housing nose cone 24. In the assembled state, the interlocking action of the interlock rib 36 with respect to the interlock ring 38 serves to securely position the housing nose cone 24 in the axial direction with respect to the housing main body 22, while the interlocking action of the interlock rib 36 with respect to the connecting leg portions 40 serves to securely position the housing nose cone 24 in the circumferential direction with respect to the housing main body 22.

The housing nose cone 24 extends rearward with cylindrical contours along the center axis to meet the inside peripheral side of the interlock ring 38, thereby defining a support cylinder portion 42 adapted for insertion into the housing main body 22. The connecting leg portions 40 which protrude up from the outside peripheral face of the housing nose cone 24 extend for prescribed distance in the axial direction until reaching the outside peripheral face of the support cylinder portion 42. A pair of cap locking projections 47, 47 formed on the inside peripheral face of the housing nose cone 24 protrude out at locations situated in opposition in the axis-perpendicular direction in proximity to the front opening.

A pair of first guide slots 44, 44 and a pair of second guide slots 46, 46 are formed extending parallel to the axial direction at locations in respectively situated in opposition in the diametrical direction on the inside peripheral face of the housing nose cone 24. Each of these first guide slots 44, 44 and second guide slots 46, 46 extends from the axially medial section of the housing nose cone 24 to the inside peripheral face of the support cylinder portion 42, and opens onto the back end of the support cylinder portion 42.

In the present embodiment in particular, the diametrical direction of opposition of the pair of first guide slots 44, 44 and the diametrical direction of opposition of the pair of second guide slots 46, 46 are orthogonal to one another. The first guide slots 44 have greater width dimension in the circumferential direction and greater depth dimension in the diametrical direction than do the second guide slots 46, and in the support cylinder portion 42 take the form of slits passing through the peripheral wall of the support cylinder portion 42.

The lancet 14 is assembled together with the housing 12 composed of the housing main body 22 and the housing nose cone 24 so as to be accommodated in the interior space thereof. The housing nose cone 24 is preferably transparent or translucent so that the collected blood is visible subsequent to puncture.

The lancet 14 is an insertion-molded component composed of a puncture needle 52 (serving as a puncture member) embedded and anchored in a rod shaped lancet hub 50 of made of synthetic resin, and extending along the center axis. The tip of the puncture needle 52 projects in the forward direction from the center of the distal end portion of the lancet hub 50.

A spring seat 54 furnished with an annular support protruding portion that extends in the circumferential direction is formed at the back end of the lancet hub 50. A pair of guide protrusions 56, 56 are integrally formed on the outside peripheral face of the back end section of the lancet hub 50 and protrude out to either side in the axis-perpendicular direction. Meanwhile, a pair of reuse-preventing protrusions 58, 58 are integrally formed on the outside peripheral face of the front end section of the lancet hub 50 and protrude out to either side in the axis-perpendicular direction. A pair of locking protrusions 60, 60 are integrally formed on the outside peripheral face of the lancet hub 50 at locations axially rearward by a prescribed dimension from the pair of reuse-preventing protrusions 58, 58, and protrude out to either side in the axis-perpendicular direction.

The direction of protrusion of the pair of reuse-preventing protrusions 58, 58 and the direction of protrusion of the pair of locking protrusions 60, 60 differ from one another. In the present embodiment in particular, the direction of protrusion of the pair of reuse-preventing protrusions 58, 58 and the direction of protrusion of the pair of locking protrusions 60, 60 differ from one another by 90 degrees about the center axis, while the direction of protrusion of the pair of reuse-preventing protrusions 58, 58 and the direction of protrusion of the pair of guide protrusions 56, 56 are the same about the center axis.

A needle cap 18 is provided to the distal end side of the lancet hub 50. The integrally formed needle cap 18 is rod-shaped and extends from the distal end of the lancet hub 50 from which the puncture needle 52 projects, along the same center axis. A twist-off portion 64 constricted to smaller outside diameter defines the boundary section of the lancet hub 50 and the needle cap 18, and is designed so that the needle cap 18 can be detached from the lancet hub 50 by a manual operation involving twisting the needle cap 18 about the center axis relative to the lancet hub 50 to induce separation at the twist-off portion 64. By detaching the needle cap 18 from the lancet hub 50, the distal end part of the puncture needle 52 that was covered by the needle cap 18 is now exposed.

Figure 6:
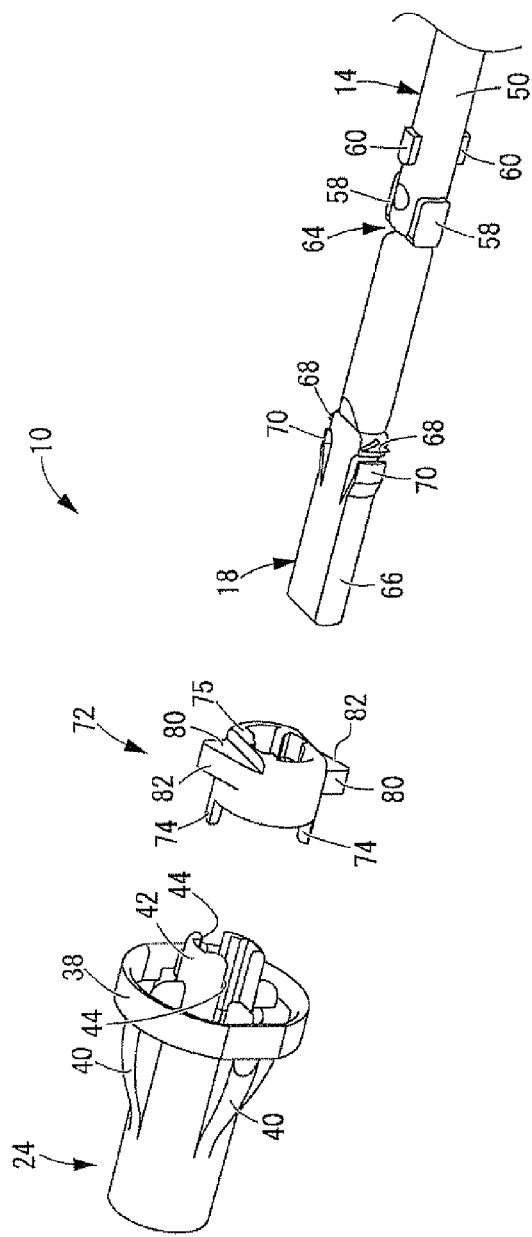
FIG. 6 is a fragmentary enlarged view of FIG. 2.
Figure 7:
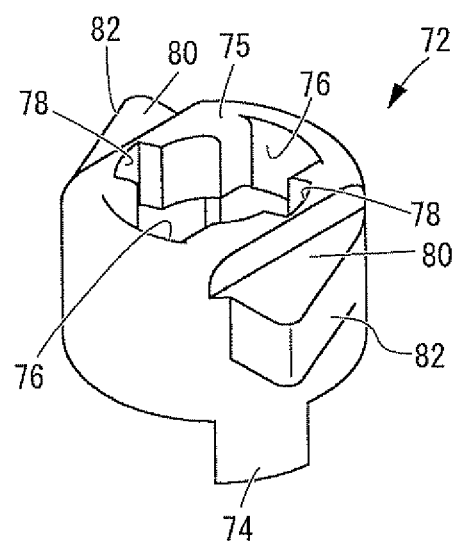
FIG. 7 is a perspective view of a locking ring of the lancing device of FIG. 1.

As depicted in FIG. 6, the distal end part of the needle cap 18 takes the form of a flattened grip portion 66; in sections to either side in the width direction of rear end section of this grip portion 66, protrusions 68 and a tongue-shaped elastic catch portions 70 are formed protruding out at locations situated in opposition in the axial direction.

The lancet 14 is inserted into the housing main body 22 from the back end of the lancet hub 50, and is assembled arranged on the center axis of the housing 12, with the needle cap 18 passing through the housing nose cone 24. During assembly of the lancet 14 with the housing 12, the compression coil spring 16 and a locking ring 72 are installed within the housing 12 as well.

Specifically, the compression coil spring 16 is accommodated within the basal portion of the housing main body 22 and arranged on the center axis with the back end portion thereof positioned fitting within the spring seat 26 of the housing main body 22, and with the front end portion mated with the spring seat 54 of the lancet hub 50. The compression coil spring 16 is thereby interposed between the axially opposed faces of the basal portion of the housing main body 22 and the back end of the lancet hub 50, and through displacement of the lancet hub 50 rearward in the axial direction (deeper into the housing main body 22) is induced to undergo compressive deformation, the urging force associated with this compressive deformation being exerted in the direction pushing the lancet hub 50 forward and out from the housing main body 22.

Meanwhile, as depicted in FIGS. 6 to 9, the locking ring 72 is a molded resin component of generally circular ring shape rotatably attached about the outside of the support cylinder portion 42 of the housing nose cone 24. A pair of abutting leg portions 74, 74 integrally formed on the locking ring 72 protrude in the forward direction, and these abutting leg portions 74, 74 insert between adjacent connecting leg portions 40, 40 along the circumference of the support cylinder portion 42. When the locking ring 72 is then rotated, the abutting leg portions 74 come into abutment against the connecting leg portions 40 in the circumferential direction, thereby limiting the permissible range of rotation of the locking ring 72 on the support cylinder portion 42 to less than 45 degrees.

An integrally formed mating portion 75 of inner flange shape is situated at the back end part of the locking ring 72; a pair of first passage slots 76, 76 and a pair of second passage slots 78, 78 are formed on the inside peripheral face of this mating portion 75 and extend parallel to the axial direction at locations respectively situated in opposition in the diametrical direction. These first passage slots 76, 76 and second passage slots 78, 78 each extend in a straight line along the entire axial length of the mating portion 75.

The inside diameter dimension of the mating portion 75 is slightly larger than the outside diameter dimension of the lancet hub 50 and the needle cap 18, and the locking ring 72 is installed fitting about the outside of the lancet hub 50 and the needle cap 18. The first passage slots 76 of the mating portion 75 have slightly larger cross section than the reuse-preventing protrusions 58 of the lancet hub 50, making it possible for the reuse-preventing protrusions 58 to travel in the axial direction through the first passage slots 76. The second passage slots 78 of the mating portion 75 have slightly larger cross section than the locking protrusions 60 of the lancet hub 50, making it possible for the locking protrusions 60 to travel in the axial direction through the second passage slots 78.

The angle (intersection angle) formed by the diametrical direction of opposition of the pair of first passage slots 76, 76 and the diametrical direction of opposition of the pair of second passage slots 78, 78 in the locking ring 72 differs from the angle (intersection angle) formed by the diametrical direction of opposition of the pair of reuse-preventing protrusions 58, 58 and the diametrical direction of opposition of the pair of locking protrusions 60, 60 on the lancet hub 50. In the present embodiment in particular, the diametrical direction of opposition of the pair of first passage slots 76, 76 and the diametrical direction of opposition of the pair of second passage slots 78, 78 intersect one another at approximately 60 degrees.

Figure 8:
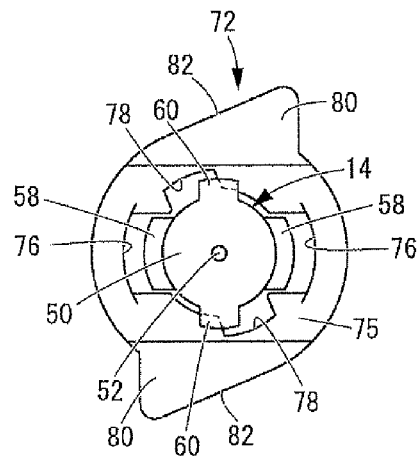
FIG. 8 is a rear view suitable for explaining action of the locking ring in the standard condition shown in FIG. 1 or in a puncture-ready condition.
Figure 9:
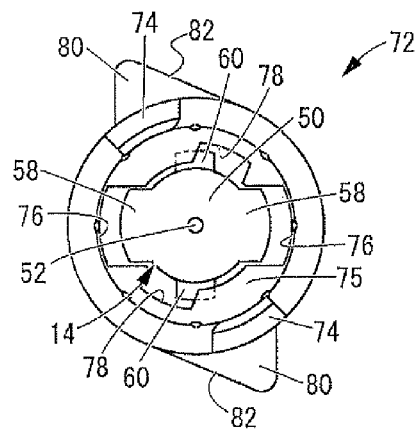
FIG. 9 is a front view suitable for explaining action of the locking ring in the standard condition shown in FIG. 1 or in the puncture-ready condition.

As will be apparent from FIGS. 8 and 9, according to this arrangement, with the lancet hub 50 passed through the locking ring 72 and the pair of reuse-preventing protrusions 58, 58 of the lancet hub 50 positioned at relative locations in the circumferential direction aligned with the pair of first passage slots 76, 76 of the locking ring 72 so as to permit passage thereof in the axial direction, the pair of locking protrusions 60, 60 of the lancet hub 50 are positioned offset from the pair of second passage slots 78, 78 of the locking ring 72, whereby the locking protrusions 60, 60 are detained by the locking ring 72 and prevented from traveling forward in the axial direction. On the other hand, with the pair of locking protrusions 60, 60 of the lancet hub 50 aligned with the pair of second passage slots 78, 78 of the locking ring 72 so as to permit passage thereof in the axial direction, the pair of reuse-preventing protrusions 58, 58 of the lancet hub 50 are positioned offset from the pair of first passage slots 76, 76 of the locking ring 72, whereby the reuse-preventing protrusions 58, 58 are detained by the locking ring 72 and prevented from traveling towards the axial rear of the lancet hub 50 relative to the locking ring 72.

The pair of reuse-preventing protrusions 58, 58 and the pair of locking protrusions 60, 60 of the lancet hub 50 are separated by a distance slightly greater than the thickness dimension of the mating portion 75 of the locking ring 72 in the direction of the center axis. Thus, with the reuse-preventing protrusions 58, 58 positioned axially forward and away from the mating portion 75 and the locking protrusions 60 positioned axially rearward and away from the mating portion 75, the locking ring 72 fitting about the outside of the lancet hub 50 is able to rotate relative to the lancet hub 50. By rotating the locking ring 72, either the pair of reuse-preventing protrusions 58, 58 or the pair of locking protrusions 60, 60 are selectively aligned with the first passage slots 76, 76 or the second passage slots 78, 78 so as to allow displacement therethrough in the axial direction.

Figure 3:
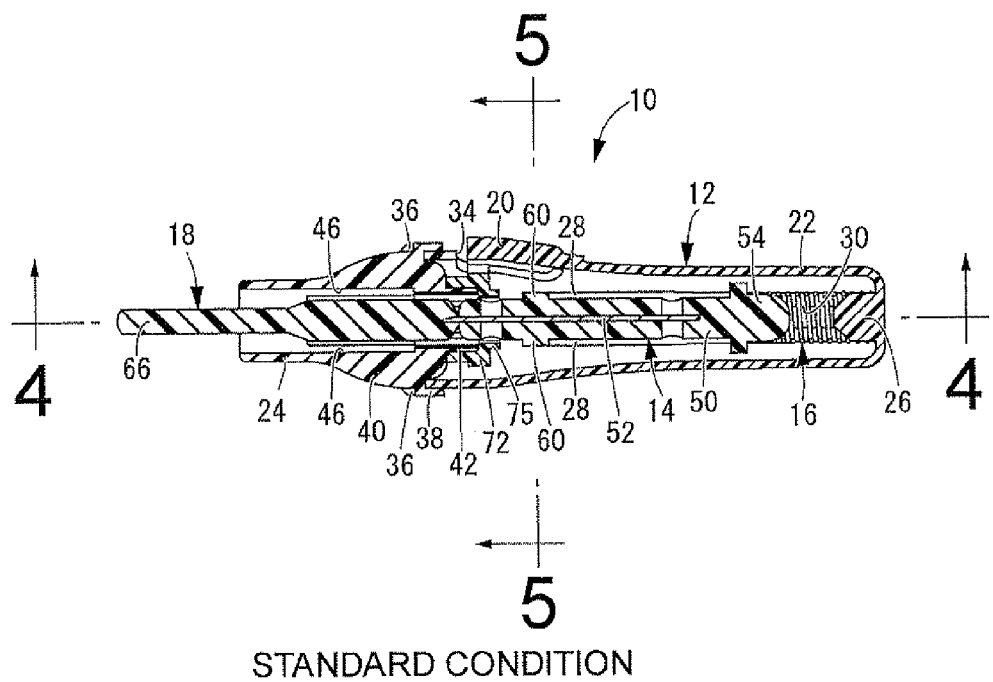
FIG. 3 is a longitudinal sectional view taken along line 3-3 of FIG. 1.
Figure 5:
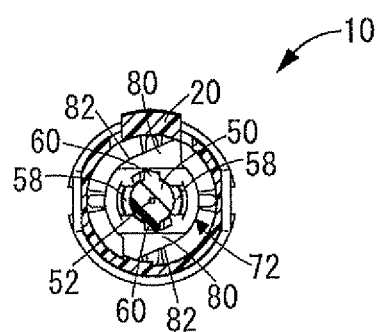
FIG. 5 is a transverse sectional view taken along line 5-5 of FIG. 3.

A pair of presser tabs 80, 80 are integrally formed on the outside peripheral surface of the locking ring 72 and protrude out to either side in the diametrical direction. The presser tabs 80 are shaped like scalene right triangles when viewed in the axial direction of the locking ring 72; the face corresponding to the diagonal face thereof constitutes a sloped pressing face 82 that is inclined about the center axis of the locking ring 72. As depicted in FIGS. 3 and 5, with the locking ring 72 installed on the support cylinder portion 42 these presser tabs 80, 80 align so as to be positioned inwardly from the operating element 20 of the housing main body 22.

The lancing device 10 of the present embodiment is assembled by installing the lancet 14, together with the compression coil spring 16 and the locking ring 72, within the housing 12 in the above manner. The guide protrusions 56, 56 that protrude from the lancet hub 50 are inserted through the guide rails 30, 30 provided as a guide mechanism for guiding the lancet 14 in the direction of extension, allowing the lancet 14 installed within the housing 12 to move in the axial direction while preventing rotation of the lancet 14 about the center axis, i.e. circumferential displacement relative to the housing 12.

Figure 4:
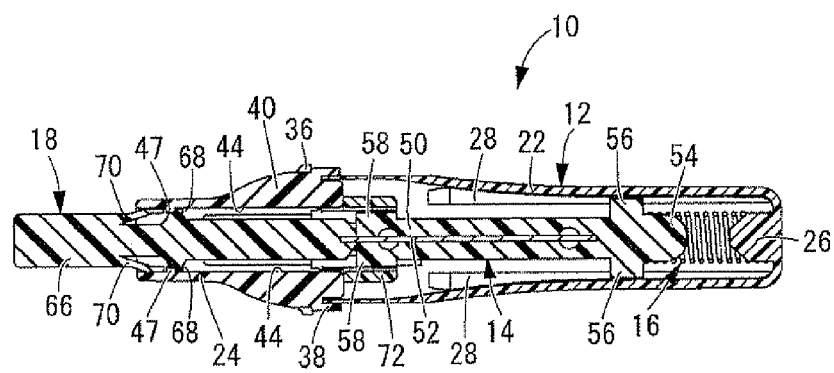
FIG. 4 is a longitudinal sectional view taken along line 4-4 of FIG. 3.

As depicted in FIG. 4, in the standard condition in which the instrument is provided as a retail product to the user, the cap locking projections 47, 47 of the housing nose cone 24 are respectively locked in place by being clasped axially between the protrusions 68 and elastic catch portions 70 formed on the needle cap 18, positioning the lancet 14 in the axial direction with respect to the housing 12 so that the grip portion 66 of the needle cap 18 projects a prescribed distance to the outside from the housing nose cone 24.

As depicted in FIG. 3, in this standard condition, the lancet 14 is pushed deeper into the housing main body 22, inducing compressive deformation of the compression coil spring 16 until the locking protrusions 60, 60 of the lancet hub 50 are positioned to the back of the locking ring 72. As depicted in FIG. 4, in this condition, the reuse-preventing protrusions 58, 58 of the lancet hub 50 are positioned straddling across the first passage slots 76, 76 of the locking ring 72 and the first guide slots 44, 44 of the support cylinder portion 42 of the housing nose cone 24. That is, this engagement of the reuse-preventing protrusions 58 within the first passage slots 76 of the locking ring 72 and the first guide slots 44 of the housing nose cone 24 constitutes an inadvertent operation prevention mechanism designed to lock the locking ring 72 nonrotatably in the circumferential direction relative to the housing nose cone 24.

As depicted in FIG. 5, in this positioned condition, the sloped pressing face 82 of the presser tab 80 of the locking ring 72 is positioned in opposition inwardly from the operating element 20. When the operating element 20 is then pushed into the housing 12 with the finger, one circumferential end of the operating element 20 presses against the sloped pressing face 82, and on the basis of component force action produced according to the slope angle of the sloped pressing face 82, the pushing force of the operating element 20 is converted to rotational force that is exerted on the locking ring 72. As mentioned earlier, in the standard condition depicted in FIGS. 3 and 4, rotation of the locking ring 72 relative to the housing 12 is prevented, and thus inadvertent actuation of the puncturing operation of the lancing device 10 is avoided even if the operating element 20 is accidentally pressed.

(Puncture-Ready Condition)

Figure 10:
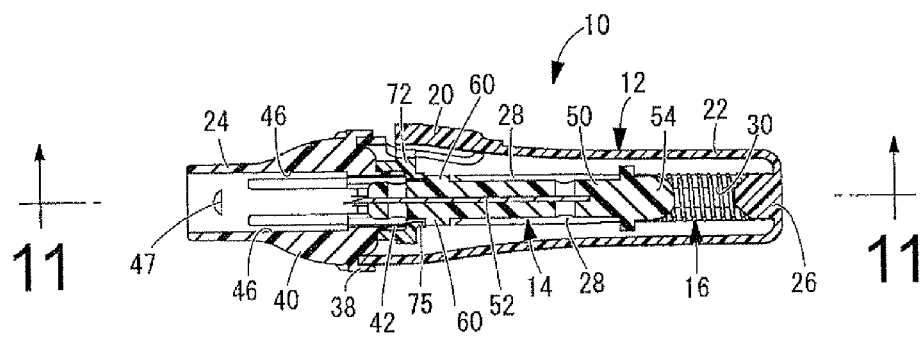
FIG. 10 is a longitudinal sectional view showing the puncture-ready condition of the lancing device of FIG. 1, corresponding to FIG. 3.
Figure 11:
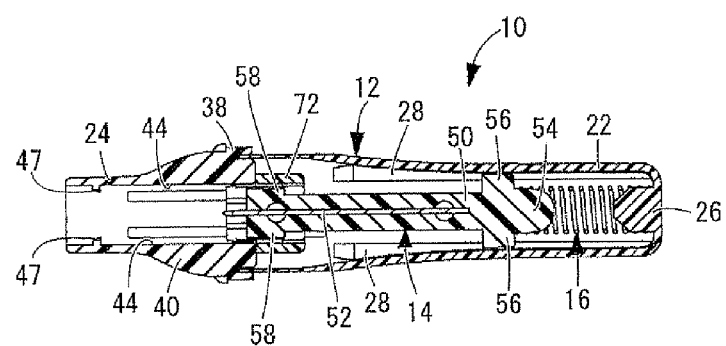
FIG. 11 is a longitudinal sectional view taken along line 11-11 of FIG. 10.

The description now turns to a discussion of the puncturing operation using the lancing device 10 provided in the standard condition discussed above. First, with the lancing device 10 in the standard condition depicted in FIGS. 3 and 4, the housing 12 is grasped in one hand while the other hand grasps the needle cap 18 and twists the needle cap 18. This causes the protrusions 68 and the elastic catch portions 70 of the needle cap 18 to disengage from the cap locking projections 47 of the housing nose cone 24, and the needle cap 18 to twist off from the lancet hub 50 at the twist-off portion 64 so that the needle cap 18 detaches from the housing nose cone 24. Through this operation, the lancing device 10 is brought from the standard condition to the puncture-ready condition depicted in FIGS. 10 and 11.

With the lancing device 10 in this puncture-ready condition, the needle cap 18 is released from being positioned in the axial direction with respect to the housing nose cone 24, and the lancet hub 50 moves axially forward under the urging force of the compression coil spring 16. The locking protrusions 60 of the lancet hub 50 come into abutment against the back end face of the mating portion 75 of the locking ring 72, preventing displacement further forward in the axial direction. This locking action of the locking protrusions 60 against the locking ring 72 maintains the lancet 14 in the puncture-ready position.

As the lancet hub 50 moves into this position, the reuse-preventing protrusions 58, 58 of the lancet hub 50 move away in the forward direction from their position of engagement in the first passage slots 76, 76 of the locking ring 72, and become positioned so as to be engaged exclusively in the first guide slots 44, 44 of the housing nose cone 24.

Thus, in the puncture-ready condition, the reuse-preventing protrusions 58, 58 and the locking protrusions 60, 60 of the lancet hub 50 disengage to the axially forward side and rearward side, respectively, of the first passage slots 76, 76 and the second passage slots 78, 78 of the locking ring 72, thereby allowing the locking ring 72 to rotate inside the housing 12.

(Puncturing Operation Condition)

Figure 12:
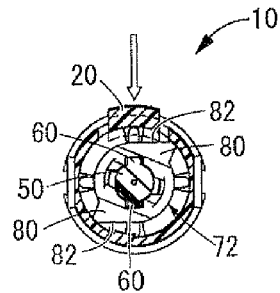
FIG. 12 is a transverse sectional view suitable for explaining a puncturing operation of the lancing device of FIG. 1, corresponding to FIG. 5.
Figure 13:
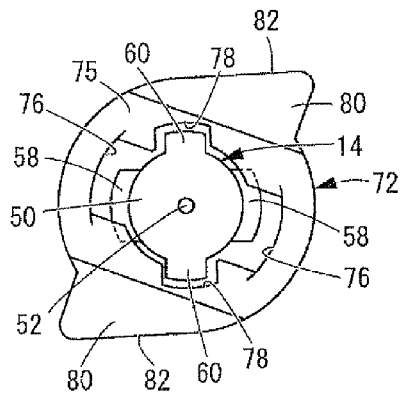
FIG. 13 is a rear view suitable for explaining action of the locking ring in the puncturing operation condition shown in FIG. 12 and in a post-puncture condition.
Figure 14:
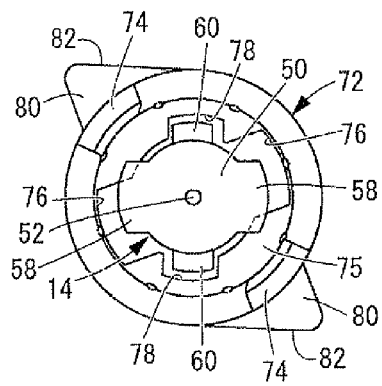
FIG. 14 is a front view suitable for explaining action of the locking ring in the puncturing operation condition shown in FIG. 12 and in the post-puncture condition.

Accordingly, to bring the instrument from the puncture-ready condition to the puncturing operation condition for the puncturing operation to take place, as depicted in FIG. 12, the operating element 20 is pushed with the finger while holding the lancing device 10 in the puncture-ready condition. By pressing in the operating element 20 against the sloped pressing face 82 of the locking ring 72, the locking ring 72 rotates about the center axis with respect to the housing 12 and the lancet 14. As depicted in FIGS. 13 and 14, when the second passage slots 78, 78 of the locking ring 72 align with the locking protrusions 60, 60 of the lancet hub 50 that were previously abutting the back end face of the locking ring 72, the locking protrusions 60, 60 are released from the condition of inhibited displacement in the axial direction by the locking ring 72, thereby allowing displacement of the locking protrusions 60, 60 in the axially forward direction through the second passage slots 78, 78 of the locking ring 72.

Figure 15:
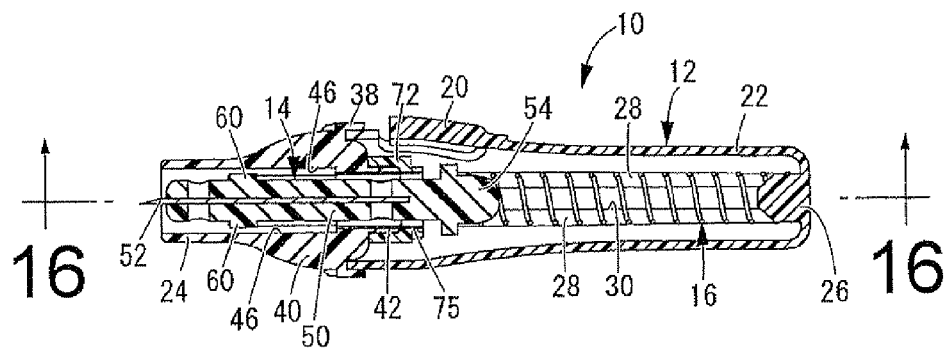
FIG. 15 is a longitudinal sectional view showing the puncturing operation condition of the lancing device of FIG. 1, corresponding to FIG. 3.
Figure 16:
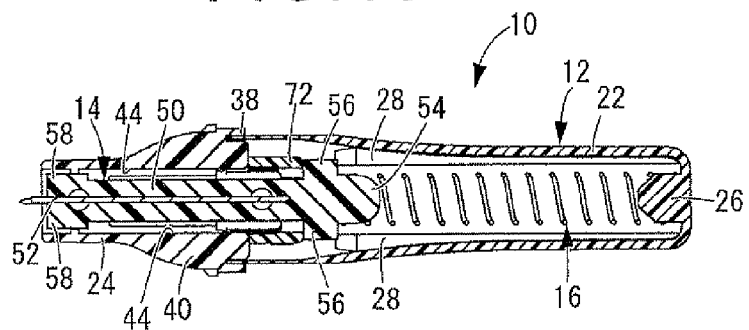
FIG. 16 is a longitudinal sectional view taken along line 16-16 of FIG. 15.

As a result, as depicted in FIGS. 15 and 16, the lancet 14 travels axially forward inside the housing 12 in a forceful manner under the urging force of the compression coil spring 16. The lancet 14 thereby travels axially forward until the guide protrusions 56, 56 of the lancet 14 come into abutment against the back end face of the locking ring 72, whereby the tip of the puncture needle 52 of the lancet 14 extends a prescribed distance outward from the front end opening of the housing nose cone 24 so that the puncturing operation may take place.

(Post-Puncture)

During the puncturing operation, owing to the urging force of the compression coil spring 16, the lancet 14 travels axially forward by a distance exceeding the free length of the compression coil spring 16. At this point, because the axial ends of the compression coil spring 16 are respectively anchored to the basal part of the housing main body 22 and the back end part of the lancet 14, at the moment of puncture at which the puncture needle 52 extends out from the housing nose cone 24, the restoring force of the compression coil spring 16 acts on the lancet 14 in the direction drawing back inside the housing 12.

Figure 17:
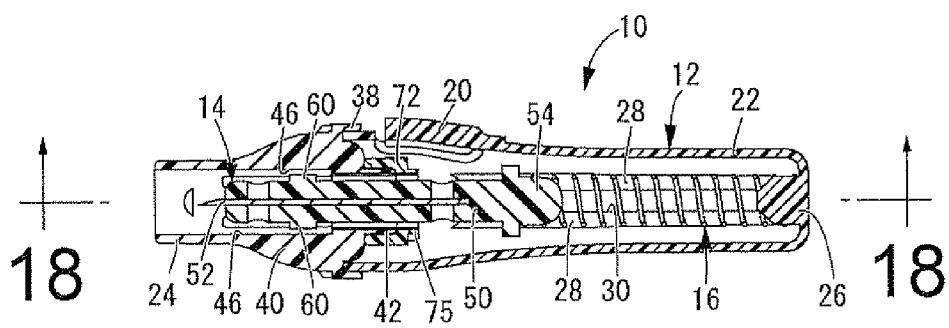
FIG. 17 is a longitudinal sectional view showing the post-puncture condition of the lancing device of FIG. 1, corresponding to FIG. 3.
Figure 18:
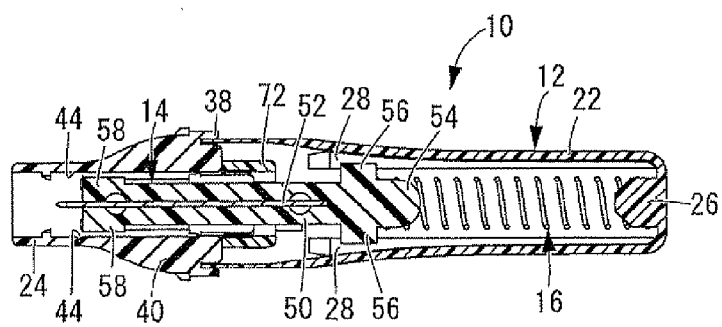
FIG. 18 is a longitudinal sectional view taken along line 18-18 of FIG. 17.

As a result, the puncturing operation of the puncture needle 52 extending out from the housing nose cone 24 takes place instantaneously, and subsequent to puncture the lancet 14 is rapidly withdrawn back inside the housing 12 and the tip of the puncture needle 52 is kept inside the housing nose cone 24, as depicted in FIGS. 17 and 18.

(Prevention of Reuse)

Subsequent to the puncturing operation described above, as depicted in FIGS. 17 and 18, the lancet 14 is retained at an axial location that is determined by the free length of the compression coil spring 16. The locking ring 72 that was previously rotated by the operating element 20 remains at its position subsequent to rotation as depicted in FIGS. 13 and 14. Specifically, subsequent to puncture, the locking ring 72 is held at a rotational position representing the unlocked state with no rotational force being exerted upon it, so even if the lancet 14 is pushed inward the locking protrusions 60 simply travel through the second passage slots 78 so that the locking protrusions 60 are not detained by the locking ring 72. Thus, subsequent to puncture, the puncturing operation to extend the lancet 14 axially forward cannot be reproduced even if the operating element 20 is operated.

Additionally, if subsequent to puncture it is attempted to forcibly reuse the instrument by pushing a piece of wire or the like through the front opening of the housing 12 to push the lancet 14 deep into the housing 12, as depicted in FIGS. 13 and 14, because the relative positions in the circumferential direction of the reuse-preventing protrusions 58, 58 and the locking protrusions 60, 60 of the lancet 14 differ from the relative positions in the circumferential direction of the first passage slots 76, 76 and the second passage slots 78, 78 of the locking ring 72, attempts at reuse can be dependably defeated.

Figure 19:
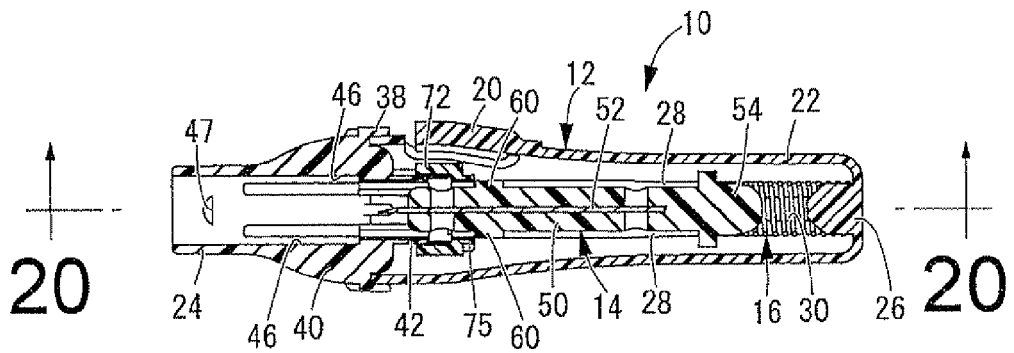
FIG. 19 is a longitudinal sectional view suitable for explaining a preventing operation of reuse of the lancing device of FIG. 1, corresponding to FIG. 3.
Figure 20:
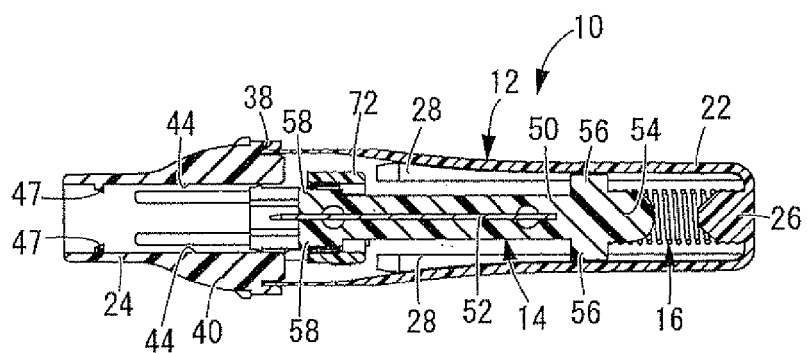
FIG. 20 is a longitudinal sectional view taken along line 20-20 of FIG. 19.

Specifically, when the lancet 14 is forcibly pushed deeper into the housing 12, even if the locking protrusions 60, 60 of the lancet 14 can be successfully aligned with the second passage slots 78, 78 in the circumferential direction so that the locking protrusions 60, 60 move deeper past the locking ring 72, at this point in time the reuse-preventing protrusions 58, 58 have already been positioned out of alignment with respect to the first passage slots 76, 76. Thus, as shown in FIGS. 19 and 20, as the lancet 14 is pushed deeper in, the reuse-preventing protrusions 58, 58 come into abutment against the front end face of the mating portion 75 of the locking ring 72 so that the locking ring 72 simply moves deeper into the housing 12 together with the lancet 14, making it substantially impossible for lancet 14 to be re-engaged by the locking ring 72 to bring about the puncture-ready condition depicted in FIGS. 8 to 11.

In the present embodiment in particular, the locking ring 72 is positioned to the back of the housing nose cone 24, and is larger in diameter than the support cylinder portion 42 of the housing nose cone 24 and positioned slipped about the outside of the support cylinder portion 42. Thus, the locking ring 72 is substantially concealed from view even if one looks in through the front opening of the housing nose cone 24, thus making it substantially impossible to bring about rotational displacement of the locking ring 72 while simultaneously pushing the lancet 14 inward through the small front opening of the housing nose cone 24.

Additionally, through the engaging action of the guide protrusions 56, 56 in the guide rails 30, 30 the lancet 14 is prevented from rotating about the center axis relative to the housing 12, so relative rotating action cannot be exerted on the locking ring 72 by rotating the lancet 14. Moreover, as noted previously, because the locking ring 72 is allowed to travel deeper into the housing main body 22, if it is attempted to rotate the locking ring 72 using a piece of wire or the like inserted through the front opening of the housing nose cone 24, it will be exceedingly difficult for the wire etc. to produce contact reaction force of the locking ring 72 in the axial direction.

While one preferred embodiment of the invention has been described in detail herein, it is to be understood that the invention should in no way be limited by the details of the illustrated embodiment. For example, FIGS. 21 to 34 illustrate a disposable lancing device 100 according to a second embodiment of the present invention, which employs a locking ring 72 having another construction. In the disposable lancing device 100 of the present embodiment, elements like those in the first embodiment shall be designated by like reference numerals and will not be discussed in detail.

Figure 21:
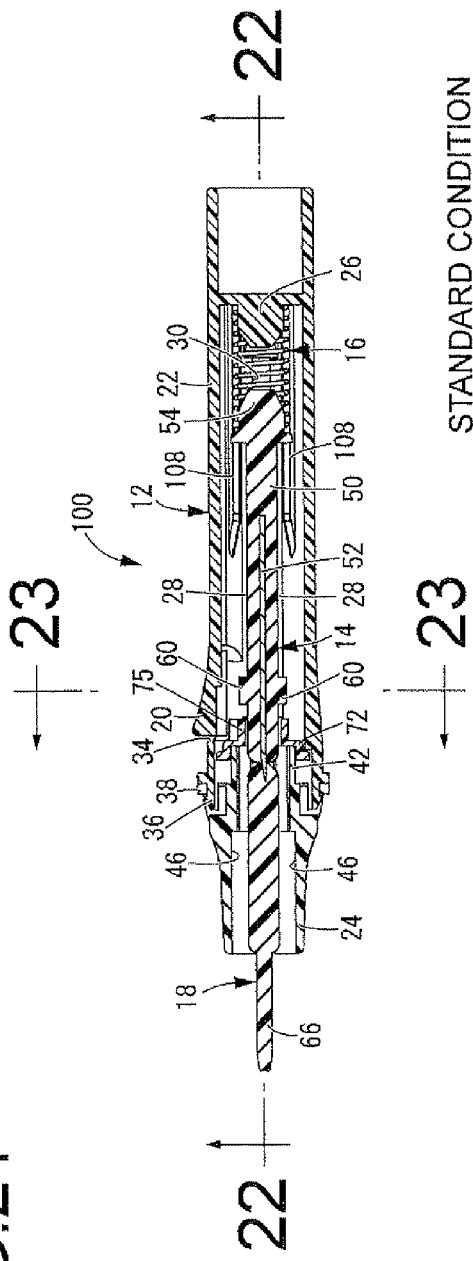
FIG. 21 is a longitudinal sectional view of a disposable lancing device according to a second embodiment of the present invention in a standard condition.
Figure 22:
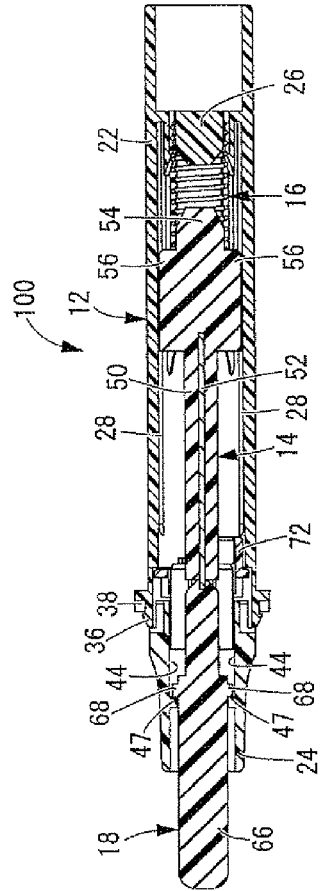
FIG. 22 is a longitudinal sectional view taken along line 22-22 of FIG. 21.
Figure 23:
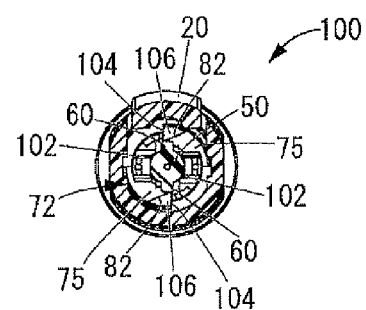
FIG. 23 is a transverse sectional view taken along line 23-23 of FIG. 21.
Figure 24:
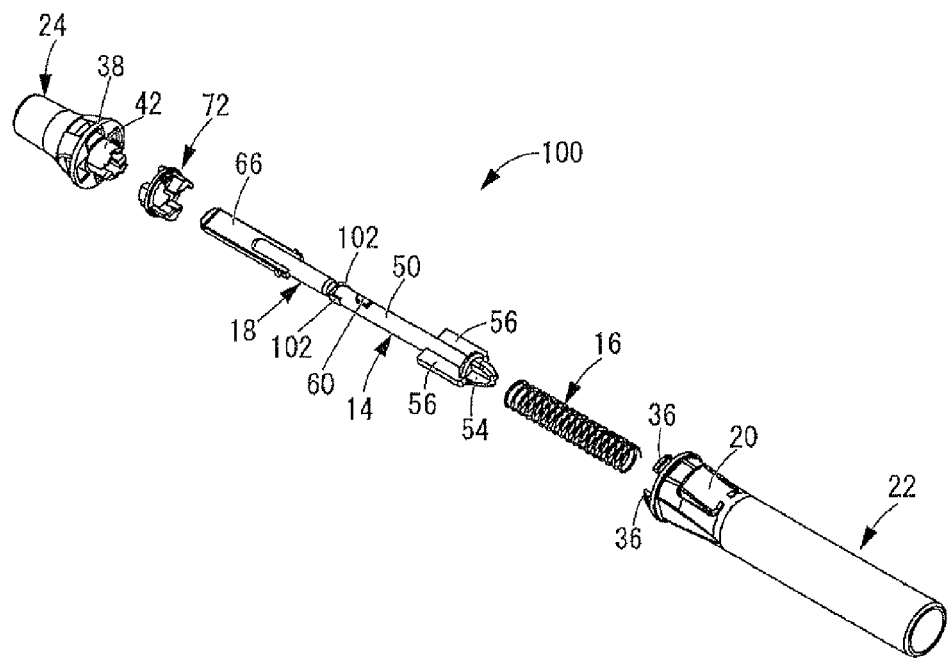
FIG. 24 is an exploded perspective view of the lancing device of FIG. 21.

FIG. 24 depicts the lancing device 100 of the present embodiment in exploded view and FIGS. 21 to 23 depict the lancing device 100 in the standard condition, namely, the retail product condition in which it is provided to the user. As seen in the drawings, in comparison with the first embodiment, the lancing device 100 is not equipped with the pair of reuse-preventing protrusions (58, 58) that protrude up from the lancet hub 50. In the present embodiment, a pair of rotation inhibiting protrusions 102, 102 are formed at approximately the same locations as the pair of reuse-preventing protrusions (58, 58) of the first embodiment.

In association therewith, the contour of the mating portion 75 of the locking ring 72 differs from that of the first embodiment. Specifically, the mating portion 75 of inner flange shape is furnished with a pair of notches 104, 104 situated in opposition in the diametrical direction and each traversing about one fourth of its periphery. Further, the thickness of the back end face of the mating portion 75 of the locking ring 72 is partially reduced so as to define a pair of thinned portions 106, 106 which are situated in opposition in the diametrical direction. By so doing, pressing faces 82 are defined by the shoulder faces located at the border of the thinned portions 106 and positioned on the back end face of the mating portion 75 of the locking ring 72. That is, the presser tabs 80, 80 in the first embodiment that protrude from the outside peripheral face of the locking ring 72 are replaced by the thinned portions 106, 106 in the present embodiment. By means of the pressing face 82 defined by the shoulder face located at the border of the thinned portion 106, component force of the pushing force of the operating element 20 provided to the housing 12 will be exerted on the locking ring 72 and serve as rotational force.

Figure 25:
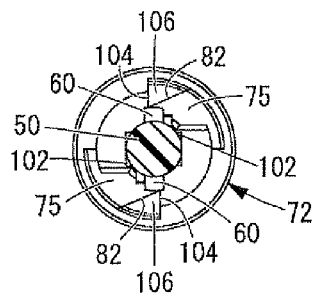
FIG. 25 is a rear view suitable for explaining action of a locking ring in the standard condition shown in FIG. 21 or in a puncture-ready condition.

In the standard condition depicted in FIGS. 21 to 23 in which the lancet 14 is positioned in the axial direction with respect to the housing 12 by engaging the needle cap 18 within the housing nose cone 24, the locking protrusions 60 are positioned axially rearward and away from the back end face of the mating portion 75 while the rotation inhibiting protrusions 102, 102 are positioned within the mating portions 75, 75 as shown in FIG. 25. In this state, both circumferential end portions of the each rotation inhibiting protrusion 102 are situated in opposition to the circumferential end portion of the each notch 104 about the center axis. With this arrangement, when the locking ring 72 rotates about the center axis, the rotation inhibiting protrusion 102 of the lancet 14 comes into abutment against the notch 104 of the mating portion 75. In addition, the lancet 14 is prevented from rotating about the center axis through insertion of its guide protrusions 56, 56 into the guide rails 30, 30 of the housing main body 22. Accordingly, in the standard condition, an inadvertent operation prevention mechanism, in which the rotation inhibiting protrusions 102, 102 come into abutment against the notches 104, 104 and the guide protrusions 56, 56 are inserted into the guide rails 30, 30 so as to be prevented from rotating about the center axis, prevents rotation of the locking ring 72 through engaging action of the locking ring 72 in the housing 12 via the lancet 14.

Figure 26:
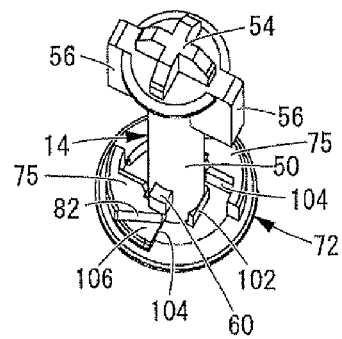
FIG. 26 is a rear perspective view suitable for explaining action of the locking ring, when the lancing device of FIG. 21 is in the puncture-ready condition.
Figure 27:
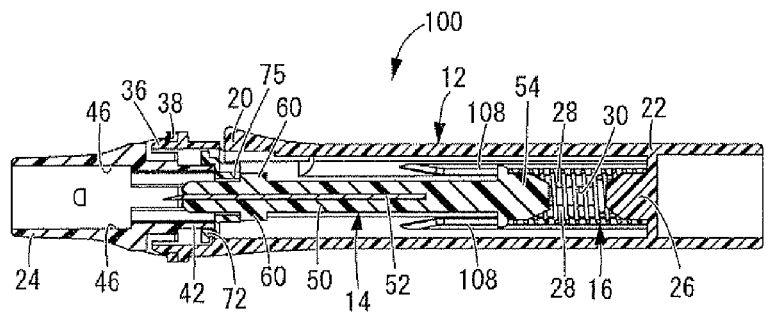
FIG. 27 is a longitudinal sectional view showing the puncture-ready condition of the lancing device of FIG. 21, corresponding to FIG. 21.

The description now turns to a discussion of the puncturing operation using the lancing device 100 provided in the standard condition discussed above. First, as in the first embodiment, the needle cap 18 is twisted off from the lancet hub 50 so that the needle cap 18 detaches from the housing nose cone 24 to bring the instrument to the puncture-ready condition as depicted in FIGS. 26 and 27. With the lancing device 100 in this puncture-ready condition, as in the first embodiment, the lancet hub 50 is released from being positioned by the needle cap 18 in the axial direction, and the lancet hub 50 moves axially forward under the urging force of the compression coil spring 16. Consequently, the locking protrusions 60, 60 of the lancet hub 50 come into abutment against the back end face of the mating portion 75 of the locking ring 72.

As the lancet hub 50 moves into this position, the rotation inhibiting protrusions 102, 102 of the lancet hub 50 move away in the forward direction from the mating portion 75 of the locking ring 72, thereby allowing the locking ring 72 to rotate inside the housing 12.

Figure 28:
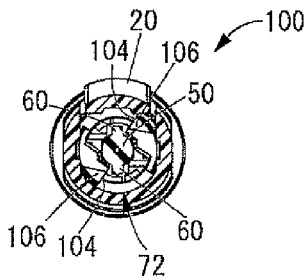
FIG. 28 is a transverse sectional view suitable for explaining a puncturing operation of the lancing device of FIG. 21, corresponding to FIG. 23.

Accordingly, in this puncture-ready condition, similar to the first embodiment, as the operating element 20 is pushed inwardly towards the housing 12, the operating element 20 is pressed against the pressing face 82 of the locking ring 72, so that the locking ring 72 rotates about the center axis with respect to the housing 12 and the lancet 14 under the component force in the rotational direction. By so doing, as depicted in FIGS. 28 to 30, when the locking protrusions 60, 60 of the lancet hub 50 that were previously abutting the back end face of the mating portion 75 of the locking ring 72 align with the notches 104, 104 of the locking ring 72, the lancet hub 50 is released from the condition of inhibited displacement in the axial direction, thereby allowing displacement of the locking protrusions 60, 60 in the axially forward direction through the notches 104, 104 of the locking ring 72.

Figure 31:
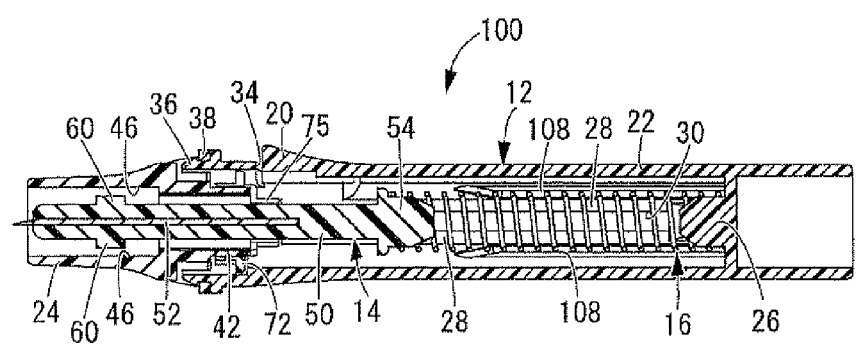
FIG. 31 is a longitudinal sectional view showing the puncturing operation condition of the lancing device of FIG. 21, corresponding to FIG. 21.

As a result, as depicted in FIG. 31, the lancet 14 travels axially forward inside the housing 12 in a forceful manner under the urging force of the compression coil spring 16. As in the first embodiment, the puncture needle 52 extends instantaneously out of the front opening of the housing 12 so that the puncturing operation may take place. In the present embodiment, a plurality of positioning ribs 108 protrude from the inside peripheral face of the tubular portion of the housing main body 22 so as to extend in the axial direction over the basal end side thereof in which the compression coil spring 16 is disposed. Owing to these plurality of positioning ribs 108, the compression coil spring 16 is able to be stably positioned along the center axis and undergo extensional and contractive deformation.

Figure 29:
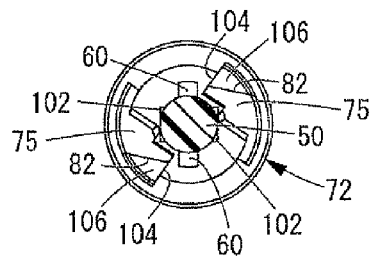
FIG. 29 is a rear view suitable for explaining action of the locking ring in the puncturing operation condition shown in FIG. 28 or in a post-puncture condition.
Figure 30:
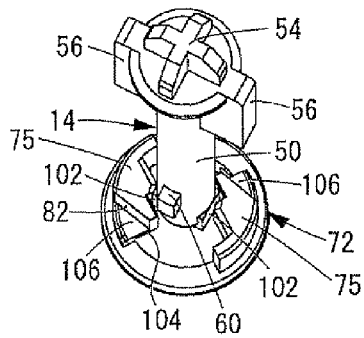
FIG. 30 is a rear perspective view suitable for explaining action of the locking ring in the puncturing operation condition shown in FIG. 28.
Figure 32:
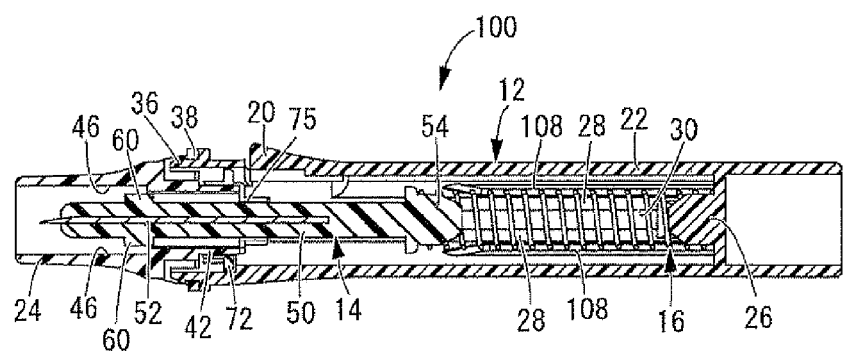
FIG. 32 is a longitudinal sectional view showing the post-puncture condition of the lancing device of FIG. 21, corresponding to FIG. 21.
Figure 33:
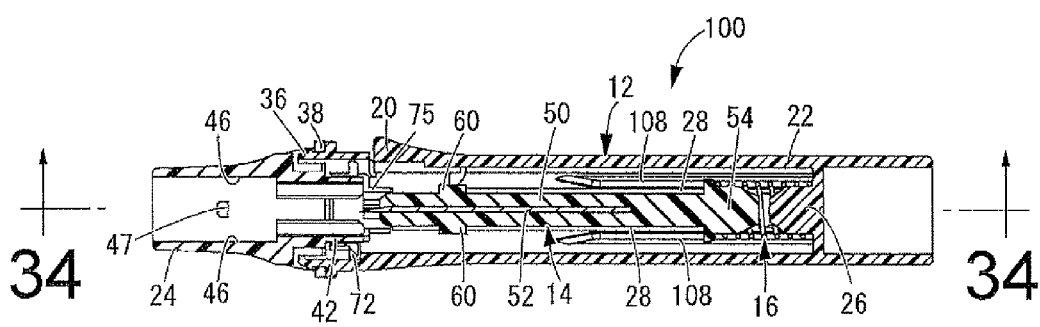
FIG. 33 is a longitudinal sectional view suitable for explaining a preventing operation of reuse of the lancing device of FIG. 21, corresponding to FIG. 21.
Figure 34:
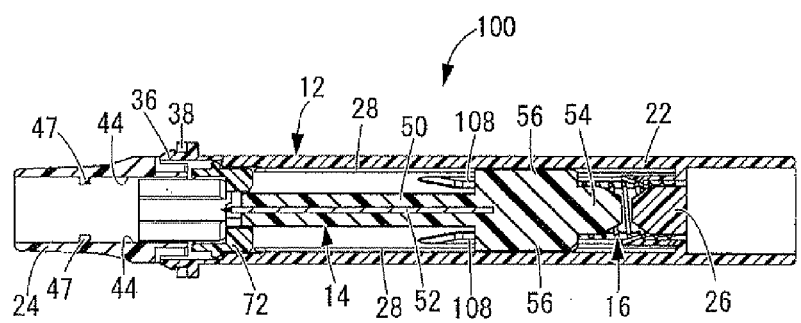
FIG. 34 is a longitudinal sectional view taken along line 34-34 of FIG. 33.

Moreover, as illustrated in FIG. 32, in the post-puncture condition in which the tip of the puncture needle 52 is kept inside the housing nose cone 24, the locking ring 72 that was previously rotated by the operating element 20 remains at its position subsequent to rotation as depicted in FIGS. 29 and 30. Thus, subsequent to puncture, even if it is attempted to forcibly reuse the instrument by pushing the lancet 14 deep into the housing 12, as depicted in FIGS. 33 and 34, the locking protrusions 60, 60 of the lancet 14 simply moves deeper into the housing main body 22 through the notches 104, 104 of the locking ring 72, making it substantially impossible for lancet 14 to be re-engaged by the locking ring 72 to bring about the puncture-ready condition depicted in FIGS. 25 to 27.

In the present embodiment in particular, because the guide protrusions 56, 56 are inserted into the guide rails 30, 30 so as to prevent the lancet 14 from rotating about the center axis with respect to the housing 12, it is also impossible for the lancet 14, which has been pushed in, to be rotated and engaged by the locking ring 72. Therefore, in order to bring about the puncture-ready condition again subsequent to puncture, it is necessary to induce rotational displacement of the locking ring 72 while simultaneously pushing the lancet 14 inward through the small front opening of the housing nose cone 24. Accordingly, it will be even more difficult to reuse the instrument.

In the lancing devices 10, 100 according to the preceding first and second embodiments, a single compression coil spring 16 is disposed within the housing 12 and adapted to exert both extending force and withdrawing-back force on the lancet 14. However, it would alternatively be acceptable for example to provide the lancet 14 with a spring member for exerting urging force in the extension direction and a spring member for exerting urging force in the withdrawing-back direction separately.

Also, with regard to the puncture member, the puncture needle 52 as shown by way of example herein may be replaced by a blade or the like.

Furthermore, in the first and second embodiments the inadvertent operation prevention mechanism which prevents the locking ring 72 from rotating with respect to the housing 12 is employed in order to prevent undesired extending action of the lancet 14 in the standard condition. However, it could instead be possible to employ an inadvertent operation prevention mechanism which is, for example, inserted within the operating element 20 and prevents displacement of the operating element 20 per se in the pushing direction towards the housing 12.

Moreover, in the preceding embodiments, the lancet 14 is engaged by the locking ring 72 with either the reuse-preventing protrusions 58 or the rotation inhibiting protrusions 102 while being engaged by the housing 12 with the guide protrusions 56 so as to lock the locking ring 72 nonrotatably with respect to the housing 12, thereby providing the inadvertent operation prevention mechanism. However, instead of employing the lancet 14 of this construction, it would also be acceptable to employ a cap 18 that is furnished with either reuse-preventing protrusions or rotation inhibiting protrusions adapted to be engaged by the locking ring 72 while being furnished with guide protrusions adapted to be engaged by the cap locking projections 47 so as to lock the locking ring 72 nonrotatably with respect to the housing 12, thereby providing an inadvertent operation prevention mechanism.

In addition, in order to prevent the locking ring 72 from inadvertently detaching from the housing nose cone 24 and moving axially rearward during the standard condition or puncture-ready condition, a protruding part may be provided to the inner face side of the operating element 20 (internal space side of the housing 12) for preventing detachment of the locking ring 72.

What is claimed is:

1. A disposable lancing device comprising:
   a housing;
   a spring member;
   a lancet having a puncture member at a distal end thereof, being housed in the housing, being configured to be prevented from rotation about a center axis thereof, and adapted to travel forward in an extension direction thereof urged by the spring member so that the puncture member extends out from the housing;
   a locking ring disposed within the housing such that the lancet is allowed to travel forward through the locking ring;
   a rotation-preventing protrusion provided to the lancet and being configured such that in an initial position of the lancet, the rotation-preventing protrusion is placed within and engaged with the locking ring in order to prevent a rotation of the locking ring in a circumferential direction relative to the housing; and that in a puncture-ready position of the lancet where the lancet travels forward from the initial position of the lancet, the rotation-preventing protrusion is placed outside the locking ring so as to allow the rotation of the locking ring in the circumferential direction relative to the housing;
   a locking protrusion provided to the lancet at a position more closer to a proximal end of the lancet than that of the rotation-preventing protrusion, and being configured such that in the puncture-ready position of the lancet, the locking protrusion is engaged by the locking ring so as to hold the lancet in the puncture-ready position located deep in the housing with the spring member being compressed; and an operating member adapted to rotate the locking ring so as to disengage the locking protrusion from the locking ring to thereby travel further forward the lancet by means of the spring member to carry out a puncturing operation.

2. The disposable lancing device according to claim 1, further comprising a cap attached to the distal end of the lancet so as to cover the puncture member, wherein the cap is detached from the lancet so that the lancet travels forward from the initial position to the puncture-ready position by means of the spring member, and the rotation-preventing protrusion is placed outside the locking ring while being disengaged from the locking ring.

3. The disposable lancing device according to claim 1, further comprising a guide mechanism for guiding the lancet in the extension direction thereof while preventing circumferential displacement of the lancet with respect to the housing.

4. The disposable lancing device according to claim 3, wherein the guide mechanism comprises a guide protrusion provided to the lancet and a guide rail provided to the housing with which the guide protrusion is engaged.

5. The disposable lancing device according to claim 1, wherein in a post puncture condition, the locking ring is located deep in the housing and the operating member is disabled to rotate the locking ring.

6. The disposable lancing device according to claim 1, wherein the rotation-preventing protrusion and the locking protrusion are formed on different circumferential positions of the lancet.

7. The disposable lancing device according to claim 6, wherein the locking ring has a first passage slot which allows the rotation-preventing protrusion to pass therethrough at one circumferential position, and has a second passage slot which allows the locking protrusion to pass therethrough at another circumferential position, and relative positions in the circumferential direction of the rotation-preventing protrusion and the locking protrusion of the lancet differ from relative positions in the circumferential direction of the first passage slot and the second passage slot of the locking ring.

* * * * *